(12) United States Patent
Yamamoto

(10) Patent No.: US 9,168,183 B2
(45) Date of Patent: Oct. 27, 2015

(54) FOLDING MACHINE AND METHOD FOR MANUFACTURING ABSORBENT ARTICLE

(75) Inventor: Hiroki Yamamoto, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 901 days.

(21) Appl. No.: 13/383,429

(22) PCT Filed: Jul. 30, 2010

(86) PCT No.: PCT/JP2010/062943
§ 371 (c)(1),
(2), (4) Date: Mar. 22, 2012

(87) PCT Pub. No.: WO2011/013821
PCT Pub. Date: Feb. 3, 2011

(65) Prior Publication Data
US 2012/0178608 A1    Jul. 12, 2012

(30) Foreign Application Priority Data

Jul. 31, 2009   (JP) .................................. 2009-180205

(51) Int. Cl.
*B31B 1/26* (2006.01)
*A61F 13/15* (2006.01)

(52) U.S. Cl.
CPC ..... *A61F 13/15747* (2013.01); *A61F 13/15772* (2013.01); *A61F 2013/15796* (2013.01)

(58) Field of Classification Search
CPC .. B29C 53/18; A61F 13/15747; B65H 45/12; B31B 1/26; B31B 1/52; B31B 1/54
USPC .......................... 493/405, 410, 417, 442, 454
See application file for complete search history.

(56) References Cited

U.S. PATENT DOCUMENTS 3,745,947 A *   7/1973   Brocklehurst ........... 112/470.05
5,080,741 A     1/1992   Nomura et al.
(Continued)

FOREIGN PATENT DOCUMENTS

CN    1386481 A    12/2002
EP     417766 A1    3/1991
(Continued)

OTHER PUBLICATIONS

Office Action issued Oct. 9, 2013, corresponds to Mexican patent application No. MX/a/2012/001316.
(Continued)

*Primary Examiner* — Stephen F Gerrity
*Assistant Examiner* — Joy N Sanders
(74) *Attorney, Agent, or Firm* — Hauptman Ham, LLP

(57) ABSTRACT

A folding machine includes a conveyance roll configured to come into contact with both a first region and the second region being flush with each other; a web guide mechanism configured to cause the first region and the second region to face each other with reference to the folding line so that an angle between the first region and the second region becomes smaller toward downstream; a press mechanism configured to press at least any one of the first region and the second region. The press mechanism changes a pressing strength on the web to change at least either a track length (first track length) in which one side edge provided on a downstream of a conveyance roll is conveyed or a track length (second track length) in which other side edge is conveyed.

20 Claims, 11 Drawing Sheets

(56) References Cited

U.S. PATENT DOCUMENTS

| | | | |
|---|---|---|---|
| 6,913,664 | B2 | 7/2005 | Umebayashi et al. |
| 6,926,654 | B2 | 8/2005 | Yamamoto et al. |
| 2002/0174930 | A1 | 11/2002 | Umebayashi et al. |
| 2005/0026760 | A1* | 2/2005 | Yamamoto et al. ............. 493/81 |
| 2010/0035740 | A1* | 2/2010 | Yamamoto ................... 493/357 |

FOREIGN PATENT DOCUMENTS

| | | |
|---|---|---|
| EP | 1504738 A2 | 2/2005 |
| EP | 1504738 B1 | 11/2007 |
| JP | 3113004 A | 5/1991 |
| JP | 2003038566 A | 2/2003 |
| JP | 20030385666 A1 | 2/2003 |
| JP | 2005046246 A | 2/2005 |
| JP | 2005046248 A | 2/2005 |

OTHER PUBLICATIONS

Office Action issued Nov. 25, 2013, corresponds to Eurasian patent application No. 201200171.

International Search Report and Written opinion for PCT/JP2010/062943 dated Nov. 2, 2010.

Office Action mailed Jun. 27, 2013 corresponds to Chinese patent application No. 201080033964.6.

Office Action mailed Jun. 4, 2013 corresponds to Japanese patent application No. 2009-180205.

Office Action dated Nov. 6, 2014, corresponding to Australian patent application No. 2010278102.

Office Action mailed Apr. 20, 2015, corresponding to Taiwanese patent application No. 099125432.

* cited by examiner

FIG. 10
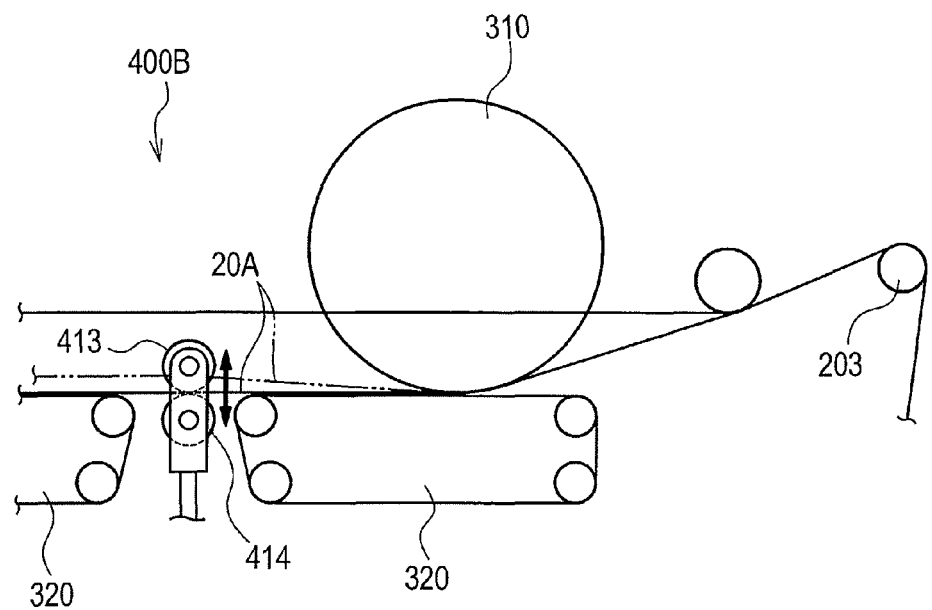
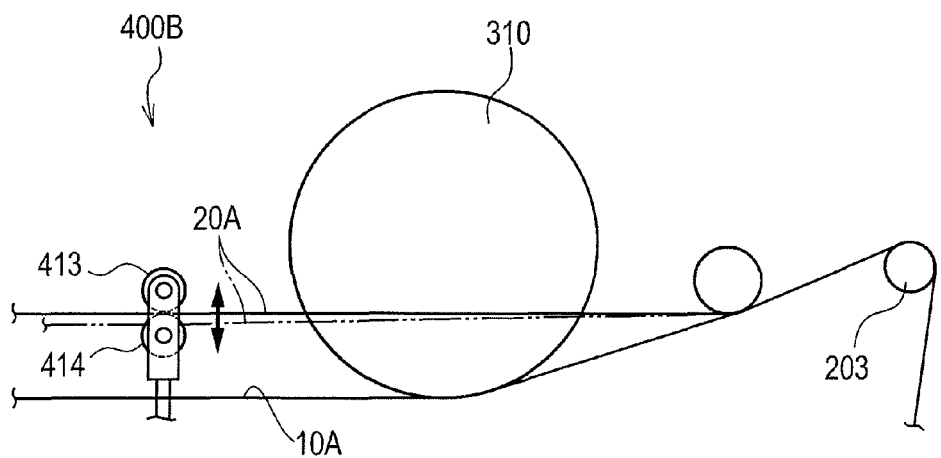

FOLDING MACHINE AND METHOD FOR MANUFACTURING ABSORBENT ARTICLE

RELATED APPLICATIONS

The present application is a National Phase of International Application Number PCT/JP2010/062943, filed Jul. 30, 2010 and claims priority from Japanese Application Number 2009-180205, filed Jul. 31, 2009.

TECHNICAL FIELD

The present invention relates to a folding machine for folding a web for an absorbent article into two and a method for manufacturing an absorbent article.

BACKGROUND ART

An absorbent article such as a pants-type disposable diaper and the like includes a front waistline portion for the wearer's front waistline, a back waistline portion for the wearer's back waistline and a crotch portion for the wearer's crotch. On each side of the crotch portions, a leg-surrounding opening portion (leg hole, for example) through which a wearer's leg is inserted is formed.

As a method for manufacturing such absorbent article, the method described below is disclosed. Specifically, stretched string-like elastic members are joined to a pair of webs (hereinafter simply referred to as "webs") in the conveyance direction (that is, in the machine direction), the webs including a continuum of the front waistline portions and a continuum of the back waistline portions. Then, a member for the crotch portion (crotch portion member) is joined to the pair of webs so that a longitudinal direction of the crotch portion member is approximately in parallel with the cross direction (CD) orthogonal to the machine direction.

Next, the web is folded into two approximately at the center of the crotch member so that a side edge of one web can be brought to overlay a side edge of the other web. Thereafter, the web is cut in the cross direction at predetermined intervals (to the size of a product) in the machine direction to form a pants-type absorbent article (refer to Patent Document 1, for example).

A machine configured to fold a pair of webs including joined crotch members into two (hereinafter referred to as "folding machine") includes at least a large-diameter roll, a folding base point bar and multiple guide rolls.

The large-diameter roll presses one of the webs. The folding position bar presses a base point for folding the webs at the folding position (approximately at the center of the crotch member) by bringing the other web toward the one web. The multiple guide rolls guide the other web toward the one web pressed by the large-diameter roll. In this configuration, the webs being supplied successively are folded into two to form pants-type absorbent articles.

In such folding machine, a sensor or the like detects positions of a side edge of one web and a side edge of the other web being conveyed, and thereby manufacture defect of the absorbent article is prevented from occurring due to a misalignment between a side edge of the one web and a side edge of the other web in the cross direction.

In a folding machine disclosed by the Patent Document 1, a side edge of one folded web is in alignment with a side edge of the other web without misalignment in the cross direction. However, there is a difference between stresses being applied to the webs.

In particular, since the one web comes into contact with the large-diameter roll and the other web come into contact with of the multiple guide rolls, stresses to be applied to the webs may differ from each other. Also, an absorbent article is asymmetric with respect to the folding position, due to factors such as differences in external appearance and stresses by the elastic members between the front waistline portion and the back waistline portion, and the arrangement position of the crotch portion member. Thus, different stresses are likely to be applied to the two webs, respectively.

As a result, the side edges of respective two webs are conveyed while following different tracks with different lengths, or are conveyed under different levels of tensions. Due to such differences, a minor phase misalignment may occur between the two webs. Here, the phase misalignment refers to a state in which the side edge of one web is aligned with the side edge of the other web after both webs are folded, but a center line in a longitudinal direction of the crotch portion member is misaligned.

According to the folding machine disclosed by the Patent Document 1, revolution speed or the like of both of the large-diameter roll and the multiple guide rolls are adjusted so that the phase misalignment falls within an allowable range according to the conveyance speed and characteristics of the webs. For this reason, when the web conveyance speed is changed or a web is replaced, for example, the phase misalignment described above might become so conspicuous as to be regarded as a product defect. Also, it is cumbersome to readjust the revolution speed or the like of the large-diameter roll and the multiple guide rolls whenever needed.

PRIOR ART DOCUMENT

Patent Document

[Patent Document 1] Patent Document 1: Japanese Patent Application Publication No. 2005-46248 (see Pages 6 to 7 and FIGS. 3 to 4)

SUMMARY OF INVENTION

A folding machine according to first aspect overlays a first region and a second region of a successively conveyed web for an absorbent article with reference to a folding line parallel with a machine direction along a flow direction of a manufacturing process for the absorbent article. The first region formed between the folding line and one side edge of the web. The second region formed between the folding line and another side edge of the web. The forming machine includes: a reference roll configured to come into contact with both the first region and the second region being flush with each other and to rotate with conveyance of the web; a web guide mechanism provided downstream of the reference roll in the machine direction, and configured to cause the first region and the second region to face each other with reference to the folding line so that an angle between the first region and the second region becomes smaller toward downstream; and a press mechanism provided downstream of the reference roll in the machine direction, and configured to press at least any one of the first region and the second region. The press mechanism changes a pressing strength on the web to change at least any one of lengths of tracks in which the one side edge and the other side edge are respectively conveyed downstream of the reference roll in the machine direction.

BRIEF DESCRIPTION OF DRAWINGS

FIG. 10 is a side view showing the vicinity of a press mechanism 400B according to a modified embodiment 2.

DESCRIPTION OF EMBODIMENTS

Next, embodiments of a folding machine and a method for manufacturing an absorbent article according to the present invention are described referring to the accompanying drawings. In the description of drawings hereinafter, same or similar signs are assigned to same or similar members. Note that the drawings are schematic and ratios of dimensions and the like are different from actual ones.

Therefore, specific dimensions and the like should be determined referring to the description given hereinafter. Moreover, the drawings also include portions having different dimensional relationships and ratios from each other.

Figure 1:
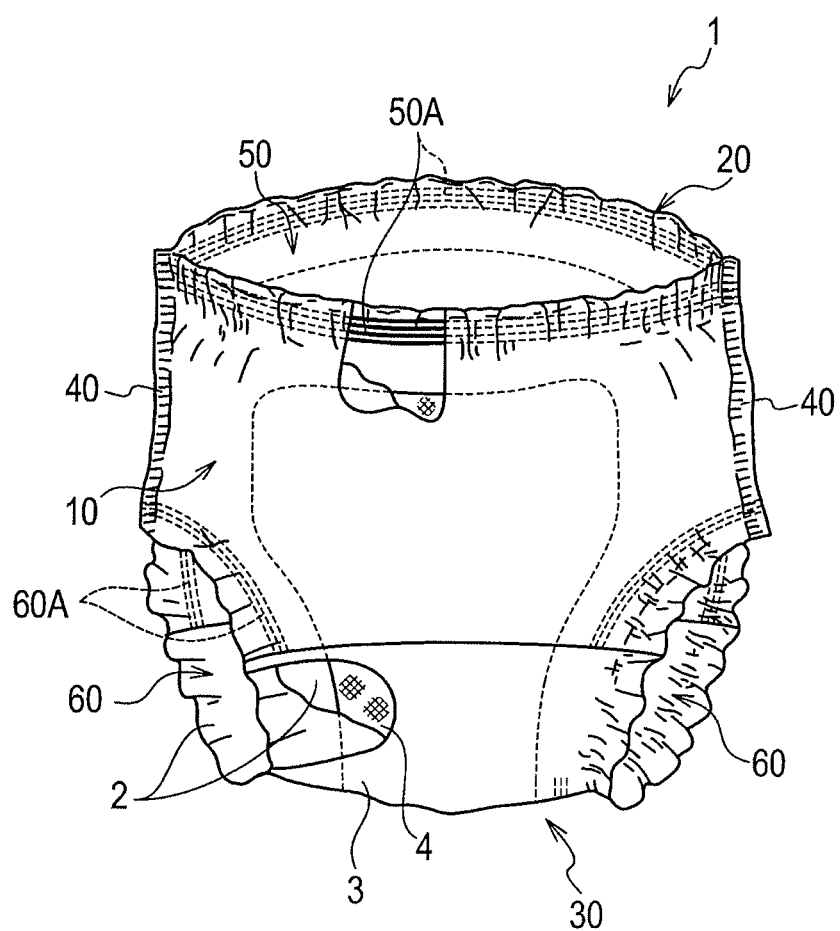
FIG. 1 is a perspective view showing an absorbent article 1 according to this embodiment.

First, with reference to the drawings, description will be provided for a configuration of an absorbent article 1 manufactured by a method for manufacturing an absorbent article using a folding machine according to the present invention. FIG. 1 is a perspective view showing the absorbent article 1 according to this embodiment.

According to this embodiment, the absorbent article 1 is a disposable pants-type diaper. As shown in FIG. 1, the absorbent article 1 mainly comprises a topsheet 2, a backsheet 3 and an absorber 4.

The topsheet 2 is provided at an innermost portion of the absorbent article 1 in contact with wear's skin. The topsheet 2 is a liquid permeable sheet made of a nonwoven fabric or a perforated plastic film, or the like. The backsheet 3 is provided at an outermost portion (on a side away from the wearer) of the absorbent article 1. The backsheet 3 is a liquid permeable sheet or the like. The absorber 4 is provided between the topsheet 2 and the backsheet 3 so as to absorb excretion discharged from the wearer. The absorber 4 is made of a mixture of ground pulp and superabsorbent polymer particles, and the like.

The absorbent article 1 thus configured is formed in combination of a front waistline portion 10 to be fitted to the wearer's front waist, a back waistline portion 20 to be fitted to the wearer's back waist, and a crotch portion 30 to be fitted to the wearer's crotch (so-called three-piece type).

The front waistline portion 10 and the back waistline portion 20 are joined together by joint portions 40, and thereby form a waist opening region 50 into which the wearer's body is inserted. A waist gather 50A formed using a string-like rubber is provided around an entire peripheral edge of a waist opening region 50.

The crotch portion 30 is provided between the front waistline portion 10 and the back waistline portion 20. A leg-surrounding opening region 60, in which an opening to insert the wearer's leg is formed, is formed on a side of the crotch portion 30. A leg gather 60A formed using a string-like rubber is provided around an entire peripheral edge of the leg-surrounding opening region 60.

Figure 2:
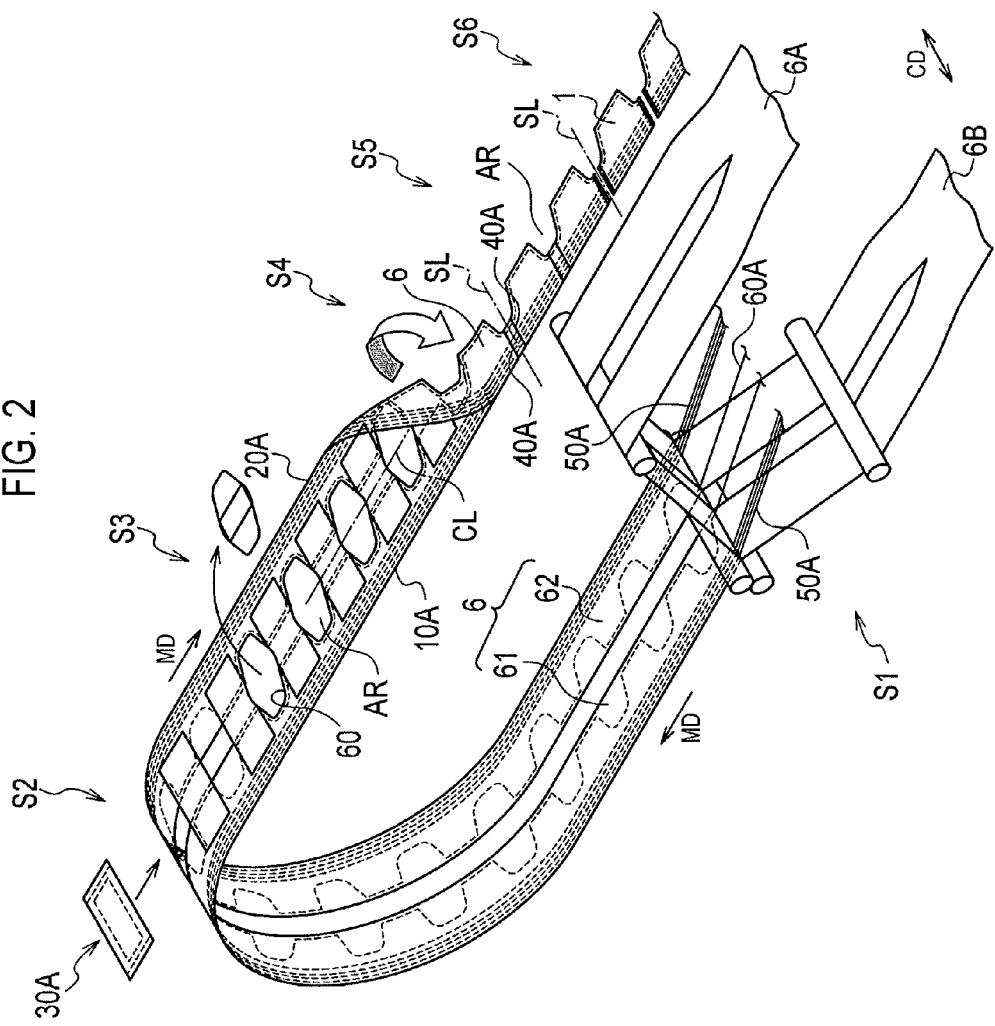
FIG. 2 is a drawing for partially illustrating a method for manufacturing an absorbent article according to this embodiment.

Next, a method for manufacturing an absorbent article according to this embodiment is described referring to the accompanying drawings. FIG. 2 is a drawing for partially illustrating the method for manufacturing an absorbent article according to this embodiment.

As shown in FIG. 2, the method for manufacturing an absorbent article includes at least a waistline portion forming step S1, a crotch portion transferring step S2, a leg-surrounding portion forming step S3, a folding step S4, a joining step S5 and a cutting step S6.

In the waistline portion forming step S1, gathers (a waist gather 50A and a leg gather 60A) are placed between a web 6A and a web 6B so as to form a pair of webs 61 and 62 respectively corresponding to the front waistline portion 10 and the back waistline portion 20.

Provided with the leg gather 60A, the webs 61 and 62 (webs 6A and 6B) can contract (extend) in a cross direction CD orthogonal to the machine direction MD along a flow direction of a manufacturing process for the absorbent article 1. Moreover, the webs 61 and 62 pass a center in the machine direction MD and are asymmetrical each other with reference to a center line CL along the machine direction MD.

In the crotch portion transferring step S2 following (downstream of) the waistline portion forming step S1, a crotch portion member 30A corresponding to the crotch portion 30 is transferred (disposed) between the pair of webs 61 and 62 at a predetermined intervals along the machine direction MD.

In the leg-surrounding portion forming step S3 following (downstream of) the crotch portion transferring step S2, a portion of the backsheet 3 made into the webs 61 and 62 (webs 6A and 6B) and the crotch portion member 30 is cut.

In the folding step S4 following (downstream of) the leg-surrounding portion forming step S3, with reference to a folding line provided at the crotch portion member 30A in parallel with the machine direction MD, a first region T1 between the folding line and a side edge 10A (side edge portion) of the web 61 and a second region T2 between the folding line and a side edge 20A (side edge portion) of the web 62 are faced each other (folded in two parts) by the folding machine 100 described below while aligning the webs each other in a predetermined positional relationship. Thus, an intermediate web 6 is obtained.

According to this embodiment, the folding line is the center line CL which passes a center of the intermediate web 6 in the cross direction CD and extends toward the machine direction MD. Moreover, the folding line may not necessarily be the center line CL, but may be shifted from the center line CL toward the side edge 10A or the side edge 20A.

Here, the folding step S4 includes a step in which either the first region T1 or the second region T2 is pressed by a press mechanism 400 described later. In this step, the pressing strength on the webs 61 and 62 is changed so as to change at least either a track length (first track length L1) in which the side edge 10A provided on a downstream of a conveyance roll 203 described later in the machine direction MD is conveyed or a track length (second track length L2) in which the side edge 20A is conveyed.

In the joining step S5 following (downstream of) the folding step S4, joint regions 40A corresponding to joint portions 40 where the front waistline portion 10 and the back waistline portion 20 are joined, are joined by ultrasonic treatment or heat treatment. The joint regions 40A are formed upstream and downstream in the machine direction MD with respect to an imaginary line SL indicating an intended cut-off position extending in the cross direction CD of the intermediate web 6.

In the cutting step S6 following (downstream of) the joining step S5, intermediate webs 6 joined at the joint area 40A are cut at predetermined intervals in the machine direction MD, that is, along the imaginary line SL, whereby individual absorbent articles 1 are manufactured.

Figure 3:
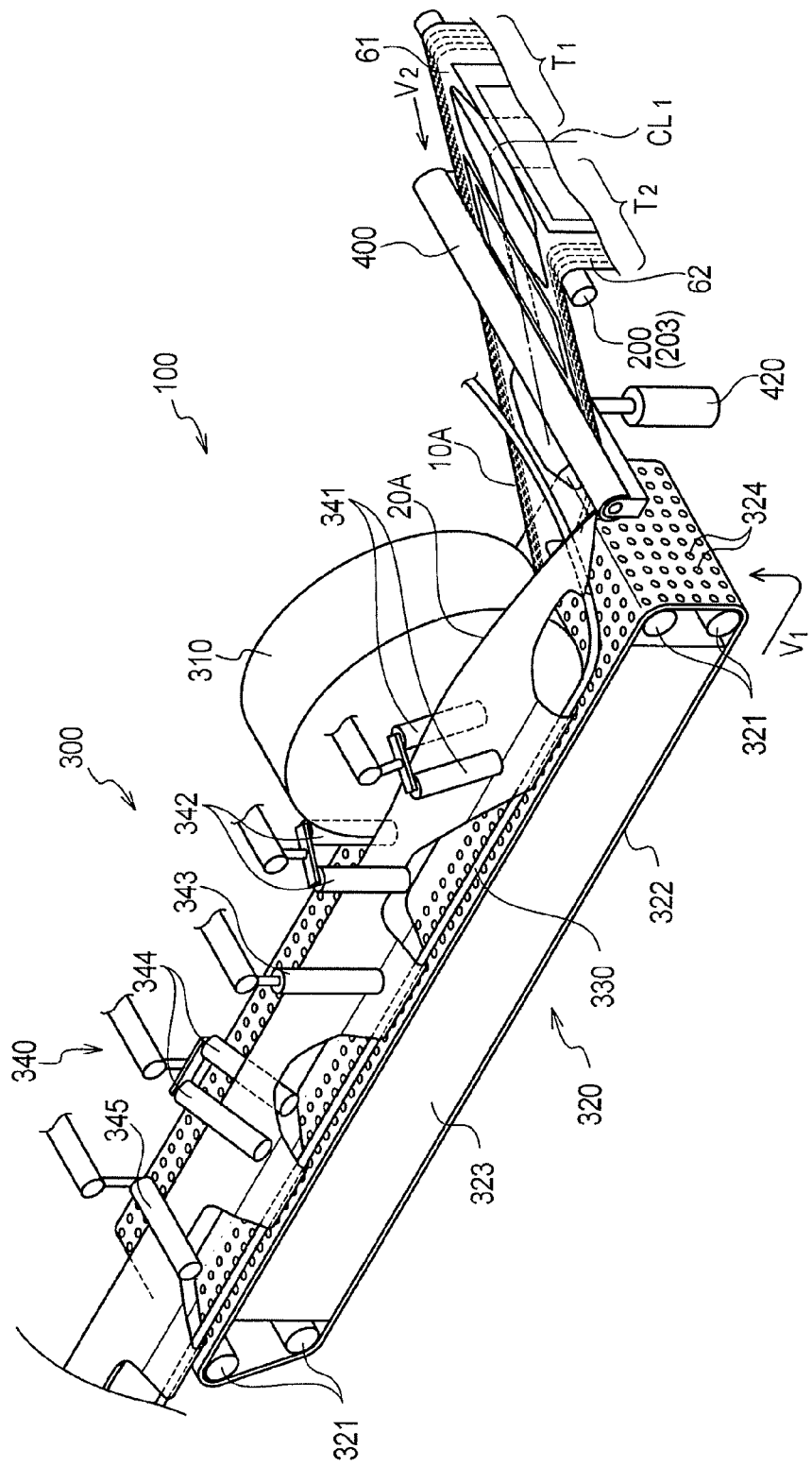
FIG. 3 is a perspective view showing a portion of a folding machine 100 according to this embodiment.
Figure 4:
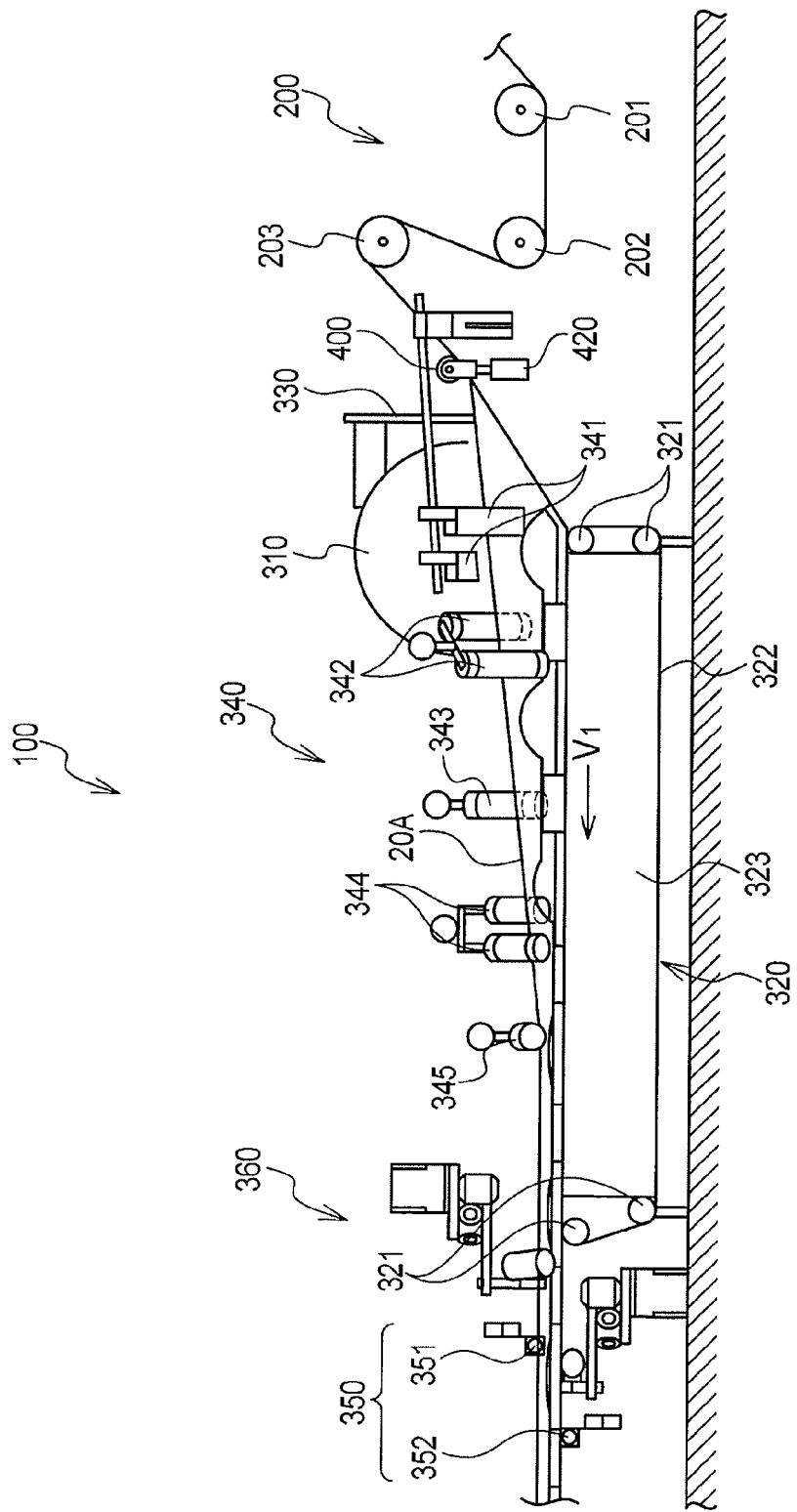
FIG. 4 is a side view showing the folding machine 100 according to this embodiment.

Next, a configuration of the folding machine 100 described above is illustrated referring to drawings. FIG. 3 is a perspective view showing the folding machine 100 according to this embodiment. FIG. 4 is a side view showing the folding machine 100 according to this embodiment.

As shown in FIG. 3 and FIG. 4, the folding machine 100 aligns and overlays the first region T1 and the second region T2 each other in a predetermined positional relationship with reference to the folding line (center line CL). The folding machine 100 comprises a conveyor roll 200, a web guide mechanism 300 and the press mechanism 400.

The conveyor roll 200 includes multiple conveyor rolls 201, 202 and 203 which rotate along the machine direction MD around a rotary shaft (not shown) provided along the cross direction CD. The conveyor roll 200 supplies the webs 61 and 62 to the web guide mechanism 300. The conveyor roll 203, which is located most close among the plurality of conveyor rolls 201, 202 and 203, to the web guide mechanism 300, is in contact with both the first region T1 and the second region T2 on a same surface and constitutes a reference roll rotating while webs 61 and 62 are being conveyed.

The web guide mechanism 300 folds the second region T2 toward the first region T1 with the first region T1 as a horizontal surface (reference surface). The web guide mechanism 300 includes a large-diameter roll 310, a belt conveyor 320, a folding base point bar 330, multiple guide rolls 340, a position detector 350 and a position controller 360.

The large-diameter roll 310 presses the web 61. The large-diameter roll 310 is provided downstream of the conveyor roll 203 in the machine direction MD. In a plan view of the webs 61 and 62 (refer to FIG. 4), the large-diameter roll 310 rotates along the machine direction MD around a rotary shaft (not shown) provided along the cross direction CD.

The large-diameter roll 310 conveys the webs 61 and 62 while pressing the first region T1 toward the belt conveyor 320. That is, the large-diameter roll 310 supports the first region T1 in an approximately horizontal state. The large-diameter roll 310 has at least a width along the cross direction CD of the first region T1.

The belt conveyor 320 conveys the first region T1 passing the large-diameter roll 310, in an approximately horizontal state. The belt conveyor 320 is provided downstream of the conveyor roll 203 in the machine direction MD, at a position opposing the large-diameter roll 310 beyond the webs 61 and 62.

The belt conveyor 320 includes multiple rolls 321, a conveyor belt 322 which is rotated around the multiple rolls 321 while supporting the first region T1, a drive means (not shown) which rotates the conveyor belt 322 around the multiple rolls 321, and a suction mechanism 323 which is capable of suctioning external air and attracts the first region T1 located on the conveyor belt 322.

Drive speed V1 of the conveyor belt 322 is preferably equal to conveyor speed V2 of the webs 61 and 62. On the conveyor belt 322, multiple suction holes 324 penetrating through the conveyor belt 322 are disposed. That is, the webs 61 and 62 are conveyed along the machine direction MD while the first region T1 is suctioned on the conveyor belt 322 by suction of the suction mechanism 323 through the suction holes 324.

The folding base point bar 330 presses a reference point where the web 62 is folded back toward the web 61 at the folding position (approximately a center of the crotch portion member 30A). That is, the folding base point bar 330 divides the first region T1 and the second region T2. The folding base point bar 330 moves from the vicinity of the conveyor roll 203 toward downstream in the machine direction MD and extends along the machine direction MD on the conveyor belt 322.

The folding base point bar 330 guides the webs 61 and 62 along the machine direction MD from the inside of the crotch portion member 30A while sliding the crotch portion member 30A. Lateral section of the folding base point bar 330 is of a circular shape. Moreover, the folding base point bar is made of a metal material and is coated with a coating material made of fluorine resin (for example, a tube made of the polytetrafluoroethylene).

The multiple guide rolls 340 guide the web 62 toward the web 61 pressed by the large-diameter roll 310. Each of the multiple guide rolls 340 includes a pair of hold rolls 341, 342, 343 and 344 and a press roll 345 (press-down mechanism). The multiple guide rolls 340 respectively rotate along the machine direction MD around a rotary shaft (not shown).

The multiple guide rolls 340 are provided downstream of the conveyor roll 203 in the machine direction MD. The multiple guide rolls 340 make the first region T1 and the second region T2 face each other (by folding into two) such that an angle between the first region T1 and the second region T2 becomes smaller gradually toward downstream from the folding line.

Here, with the side edge 10A of the web 61 and the side edge 20A of the web 62 aligned with each other in a predetermined positional relationship, the press roll 345 presses at least one of the first region T1 and the second region T2. The press roll 345 is provided most downstream in the machine direction MD of the multiple guide rolls 340. The press roll 345 rotates along the machine direction MD around a rotary shaft (not shown) provided along the cross direction CD.

The position detector 350 detects positions where the side edge 10A of the web 61 and the side edge 20A of the web 62 are conveyed. The position detector 350 is provided downstream of the multiple guide rolls in the machine direction MD. The position detector 350 includes a camera 351 and a camera 352.

The camera 351 detects (photographs) a position where the side edge 10A of the web 61 is being conveyed. On the other hand, the camera 352 detects (photographs) a position where the side edge 20A of the web 62 is being conveyed. The cameras 351 and 352 respectively transmit position data indicating detected positions where the side edges 10A and 20A are being conveyed to the position controller 360.

The position controller 360 compares position data detected by the position detector 350 with predetermined position data and, when positions where the side edges 10A and 20A are conveyed are shifted in the cross direction CD, makes alignment of tracks where the side edges 10A and 20A with each other are conveyed. Thereby the position controller 360 aligns the side edges 10A and 20A in the cross direction CD. The position controller 360 is provided downstream of the guide roll 340 in the machine direction MD and includes rolls and the like pressing the webs 61 and 62.

The press mechanism 400 presses at least one of the first region T1 and the second region T2 so as to overlay the first region T1 and the second region T2 each other. The press mechanism 400 is provided downstream of the conveyor roll 203 in the machine direction MD. Specifically, the press mechanism 400 is provided between the conveyor roll 203 and the press roll 345, that is, between the conveyor roll 203 and the large-diameter roll 310. Details of the press mechanism 400 are described later.

Figure 5:
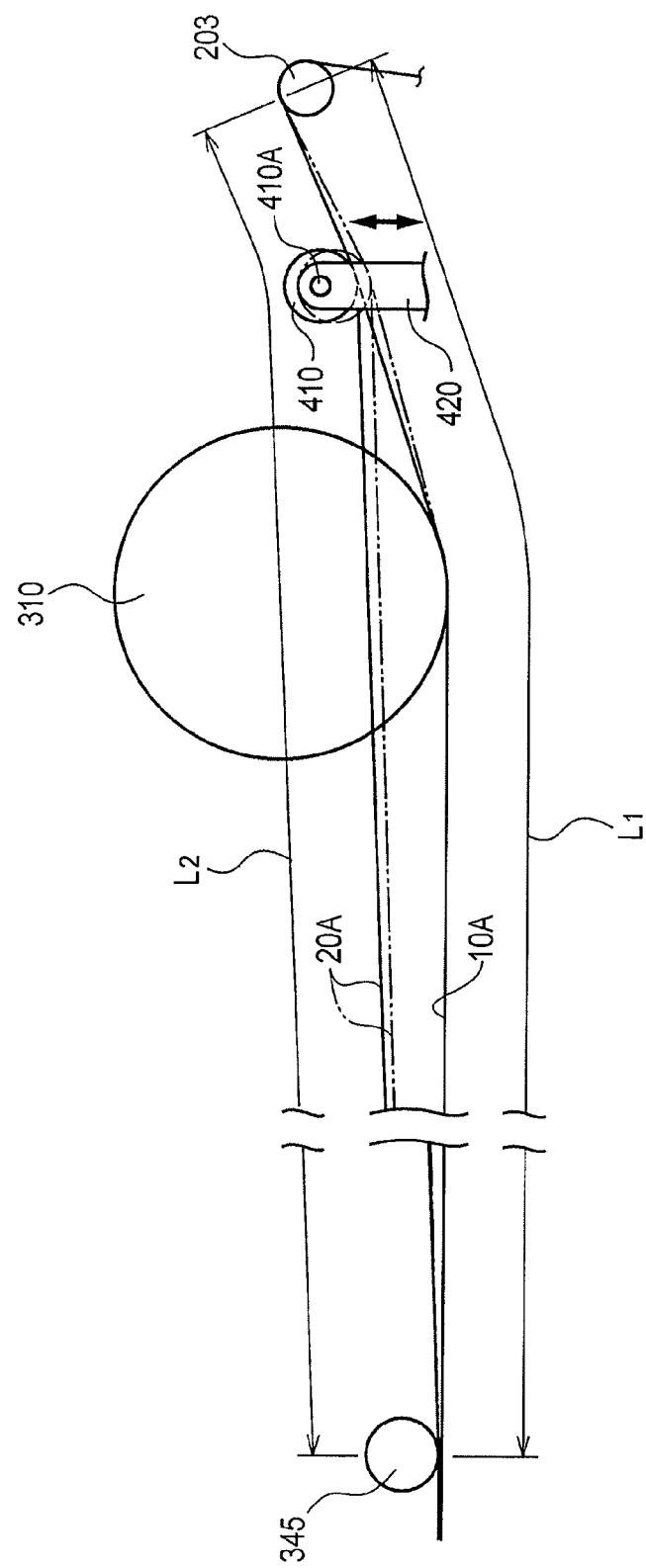
FIG. 5 is a side view showing the vicinity of a press mechanism 400 according to this embodiment.
Figure 6:
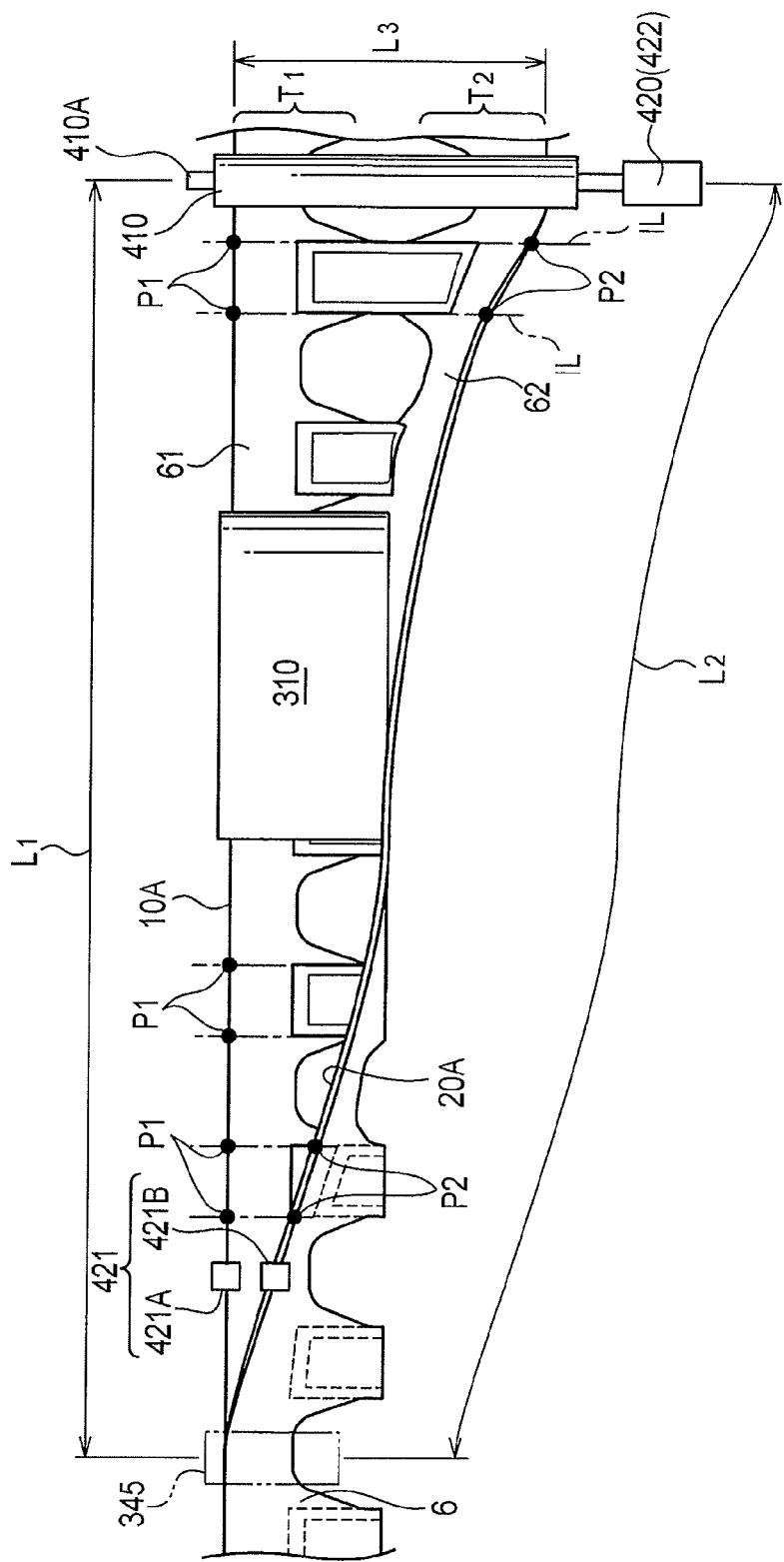
FIG. 6 is a side view showing the vicinity of the press mechanism 400 according to this embodiment.

Next, a configuration of the press mechanism 400 described above is illustrated referring to drawings. FIG. 5 is a side view showing the vicinity of the press mechanism 400 according to this embodiment. FIG. 6 is a plan view showing the vicinity of the press mechanism 400 according to this embodiment.

As shown in FIG. 5 and FIG. 6, the press mechanism 400 changes the pressing strength on the webs 61 and 62 so as to change at least either a length of a track downstream of the conveyor roll 203 in the machine direction MD where the side edge 10A is conveyed (hereinafter referred to as "first track length L1"), or a length of a track downstream of the conveyor roll 203 in the machine direction MD where the side edge 20A is conveyed (hereinafter referred to as "second track length L2"). According to this embodiment, the press mechanism 400 changes both the first track length L1 and the second track length L2 between the conveyor roll 203 and the press roll 345.

The press mechanism 400 includes a variable roll 410 and a position changer 420. According to this embodiment, the variable roll 410 comes into contact with both the first region T1 and the second region T2 on a same surface.

In a plan view of the webs 61 and 62 (refer to FIG. 6), the variable roll 410 has a central axis 410A parallel with the cross direction CD and with surfaces of the webs 61 and 62. The variable roll 410A rotates along the machine direction MD around the central axis 410A. The variable roll 410 has a length L3 along the cross direction CD of the webs 61 and 62, that is, a length longer than a length along the cross direction CD from the side edge 10A to the side edge 20A. Obviously, the variable roll 410 may be a driving roll or non-driving roll.

The position changer 420 changes a position of the variable roll 410. The position changer 420 moves around the central axis 410A of the variable roll 410. According to this embodiment, the position changer 420 moves up and down around the central axis 410A, in an axial view of the central axis 410A of the variable roll 410 (refer to FIG. 5).

The position changer 420 includes a track detector 421 and a track controller 422. The track detector 421 detects the first track length L1 and the second track length L2 between the conveyor roll 203 and the press roll 345.

The track detector 421 is provided between the conveyor roll 203 and the press roll 345. The track detector 421 includes cameras 421A and 421B.

The camera 421A detects (photographs) a predetermined position at the side edge 10A (for example, an imaginary point P1 in FIG. 6). On the other hand, the camera 421B detects (photographs) a predetermined position at the side edge 20A (for example, an imaginary point P2 in FIG. 6). The cameras 421A and 421B respectively transmit position data indicating a respectively detected position to the track controller 422.

The track controller 422 includes a cylinder and the like which are capable of sliding the central axis 410A of the variable roll 410 up and down. When the track controller 422 determines from the position data detected by the track detector 421 that a predetermined position (the imaginary point P1) at the side edge 10A is shifted with a predetermined position (the imaginary point P2) at the side edge 20A in the machine direction MD, the track controller 422 controls a movement of the central axis 410A of the variable roll 410.

Figure 7:
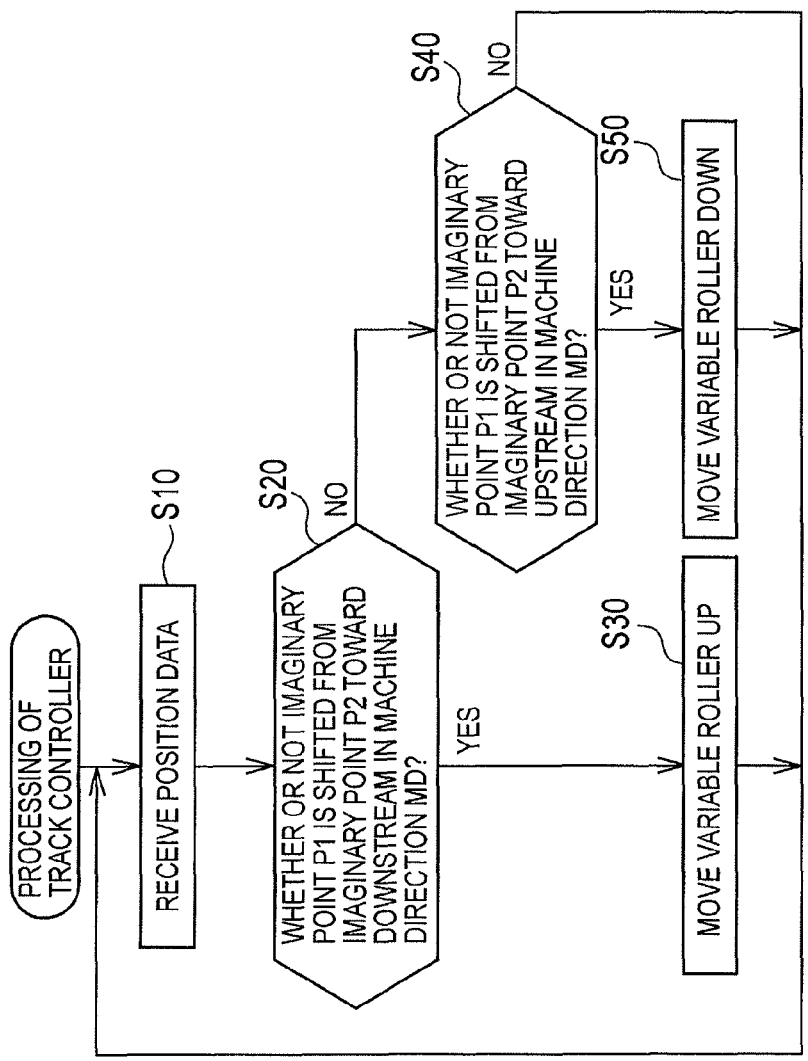
FIG. 7 is a flow chart for illustrating the processing of a track controller 422 according to this embodiment.
Figure 8:
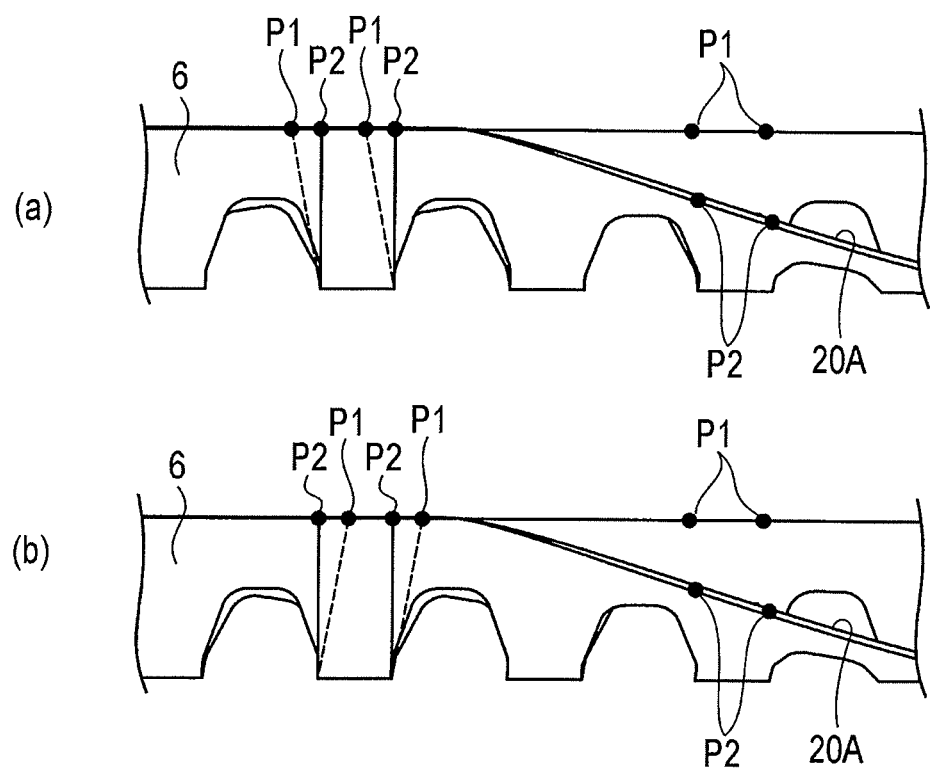
FIG. 8 is a schematic diagram showing a side edge 10A of a web 61 and a side edge 20A of a web 62 according to this embodiment.

Next, the processing of the track controller 422 described above is illustrated referring to FIG. 7. Note that FIG. 7 is a flow chart for describing the processing of the track controller 422 according to this embodiment. FIG. 8 is a schematic diagram showing the side edge 10A of the web 61 and the side edge 20A of the web 62 according to this embodiment.

Here, in the folding step S4, a phase misalignment may occur between the webs 61 and 62. The phase misalignment is a situation where the central lines TL along the longitudinal direction of the crotch portion member 30A are not aligned after the webs 61 and 62 are folded each other, in spite that the side edge 10A of the web 61 and the side edge 20A of the web 62 are aligned in the cross direction.

For example, the phase misalignment is a misalignment in which the backsheet 3 or front waistline portion 10 of the absorber 4 and the backsheet 3 or the back waistline portion 20 of the absorber 4 are not aligned with each other with respect to the machine direction MD. According to this embodiment, the phase misalignment is a misalignment in which the imaginary point P1 on the side edge 10A of the web 61 and the imaginary point P2 on the side edge 20A of the web 62 are not aligned with each other on the imaginary line IL passing a line along the cross direction CD of the absorber 4 (refer to FIG. 6 and FIG. 8).

As shown in FIG. 7, in the step S10, the track controller 422 receives position data (imaginary points P1 and P2) detected by the track detector 421.

In the step S20, the track controller 422 determines whether or not the imaginary point P1 is shifted from the imaginary point P2 toward downstream in the machine direction MD. As shown in FIG. 8(a), when the track controller 422 determines that the imaginary point P1 is shifted from the imaginary point P2 toward downward in the machine direction MD, the track controller 422 proceeds to the processing of the step S30. On the other hand, if the track controller 422 determines that the imaginary point P1 is not shifted from the imaginary point P2 toward downward in the machine direction MD, the track controller 422 proceeds to the processing of the step S40.

In the step S30, the track controller 422 moves to upstream of the central line 410A of the variable roll 410 according to the amount of misalignment between the imaginary points P1 and P2 so as to align the imaginary points P1 and P2 each other.

In the step S40, the track controller 422 determines whether or not the imaginary point P1 is shifted from the imaginary point P2 toward upward in the machine direction MD. As shown in FIG. 8(b), when the tracking controller 422 determines that the imaginary point P1 is shifted from the imaginary point P2 toward upward in the machine direction MD, the track controller 422 proceeds to the processing of the step S50. On the other hand, if the track controller 422 determines that the imaginary point P1 is not shifted from the imaginary point P2 toward upward in the machine direction MD, the track controller 422 ends the processing.

In the step S50, the track controller 422 moves to downstream of the central axis 410A of the variable roll 410 according to the amount of misalignment between the imaginary points P1 and P2 so as to align the imaginary points P1 and P2 each other.

According to this embodiment described above, the press mechanism 400 is configured to change the pressing strength on the webs 61 and 62 so as to change at least either the first track length L1 or the second track length L2. Thus, even when a minor phase misalignment occurs between the side edge 10A of the web 61 and the side edge 20A of the web 62 in the folding step S4, the phase misalignment can be easily adjusted by changing the pressing strength at which the press mechanism 400 presses the webs 61 and 62. That is, the revolution speed of the large-diameter roll and the multiple guide rolls do not need adjusting unlike a conventional folding machine. Consequently, adjustment of the phase misalignment can be simplified according to the conveyance speed and characteristics of the webs 61 and 62, and thereby degradation in the manufacture quality of the absorbent article 1 can be suppressed positively.

According to this embodiment, the press mechanism 400 includes the variable roll 410 and the position changer 420. In such configuration, the central axis 410A of the variable roll 410 is adjusted so that the variable roll 410 changes the pressing strength on the webs 61 and 62 and thereby changes at least either the first track length L1 or the second track length L2. Thus, with a simple configuration, the press mechanism 400 realizes simplified adjustment of the phase misalignment.

According to this embodiment, the variable roll 410 is provided between the conveyor roll 203 and the web guide mechanism 300. Meanwhile, in the folding step S4, alignment of the side edge 10A of the web 61 and the side edge 20A of the web 62 in the cross direction CD is performed by the position controller 360. Thus, if the variable roll 410 is provided downstream of the web guide mechanism in the machine direction MD, setting of the alignment of the side edges 10A and 20A in the cross direction CD must be changed. However, since the variable roll 410 is provided between the conveyor roll 203 and the web guide mechanism 300, the phase misalignment can be adjusted without changing the alignment setting of the side edges 10A and 20A in the cross direction CD.

According to this embodiment, the variable roll 410 has a length L3 along the cross direction CD of the webs 61 and 62 and comes into contact with both the first region T1 and the second region T2 on a same surface. Thereby, increase in the difference between the first track length L1 and the second track length L2 can be suppressed during the phase misalignment adjustment, compared with a case where the variable roll 410 changes either the first track length L1 or the second track length L2. For this reason, during the phase misalignment adjustment, a phase misalignment between the side edge 10A of the web 61 and the side edge 20A of the web 62 is unlikely to occur and the phase misalignment adjustment can be performed more easily.

Furthermore, when only either the first region T1 or the second region T2 is adjusted, the difference of stress acting on one region of either the webs 61 or 62 and another region of either the webs 61 and 62 may increase, causing a defect such as a wrinkle on either the webs 61 or 62. However, the stress difference between the webs 61 and 62 is unlikely to occur by adjusting both the first region T1 and the second region T2, whereby occurrence of a defect such as a wrinkle on the webs 61 and 62 can be prevented.

According to this embodiment, the position changer 420 includes the track detector 421 and the track controller 422, wherein the track controller 422 determines a phase misalignment from a predetermined position in the side edge 10A (imaginary point P1) and a predetermined position in the side edge 20A (imaginary point P2). Thus, when a minor phase misalignment occurs between the side edge 10A of the web 61 and the side edge 20A of the web 62, the track controller 422 immediately changes the first track length L1 and the second track length L2. Therefore, occurrence of a manufacture defect in the absorbent article 1 can be suppressed and degradation in the manufacturing quality of the absorbent article 1 can be suppressed positively. Moreover, the position changer 420 can automatically adjust a phase misalignment during manufacturing of the absorbent article 1, thereby eliminating necessity to make phase misalignment adjustment by stopping the manufacturing line.

According to this embodiment, the press mechanism 400 overlays the first region T1 and the second region T2 each other by pressing at least either the first region T1 or the second region T2. Thereby, the intermediate web 6 is conveyed to a next step (joining step S5) with the phase misalignment adjusted, so that re-occurrence of a phase misalignment after adjustment can be suppressed.

According to this embodiment, the web guide mechanism 300 folds the second region T2 toward the first region T1 with the first region T1 as a horizontal surface (reference surface), wherein a phase misalignment is likely to occur in the second region T2, so that the phase misalignment can be concentrated onto the second region T2. Consequently, the phase misalignment may be adjusted mainly in the second region T2, making the phase misalignment adjustment easier.

Modified Embodiment

Next, a modified embodiment of the press mechanism 400 according to the embodiment described above is illustrated referring to drawings. Note that same portions as those of the press mechanism 400 according to the embodiment described above are denoted with same signs, and description is focused on different portions.

Modified Embodiment 1

Figure 9:
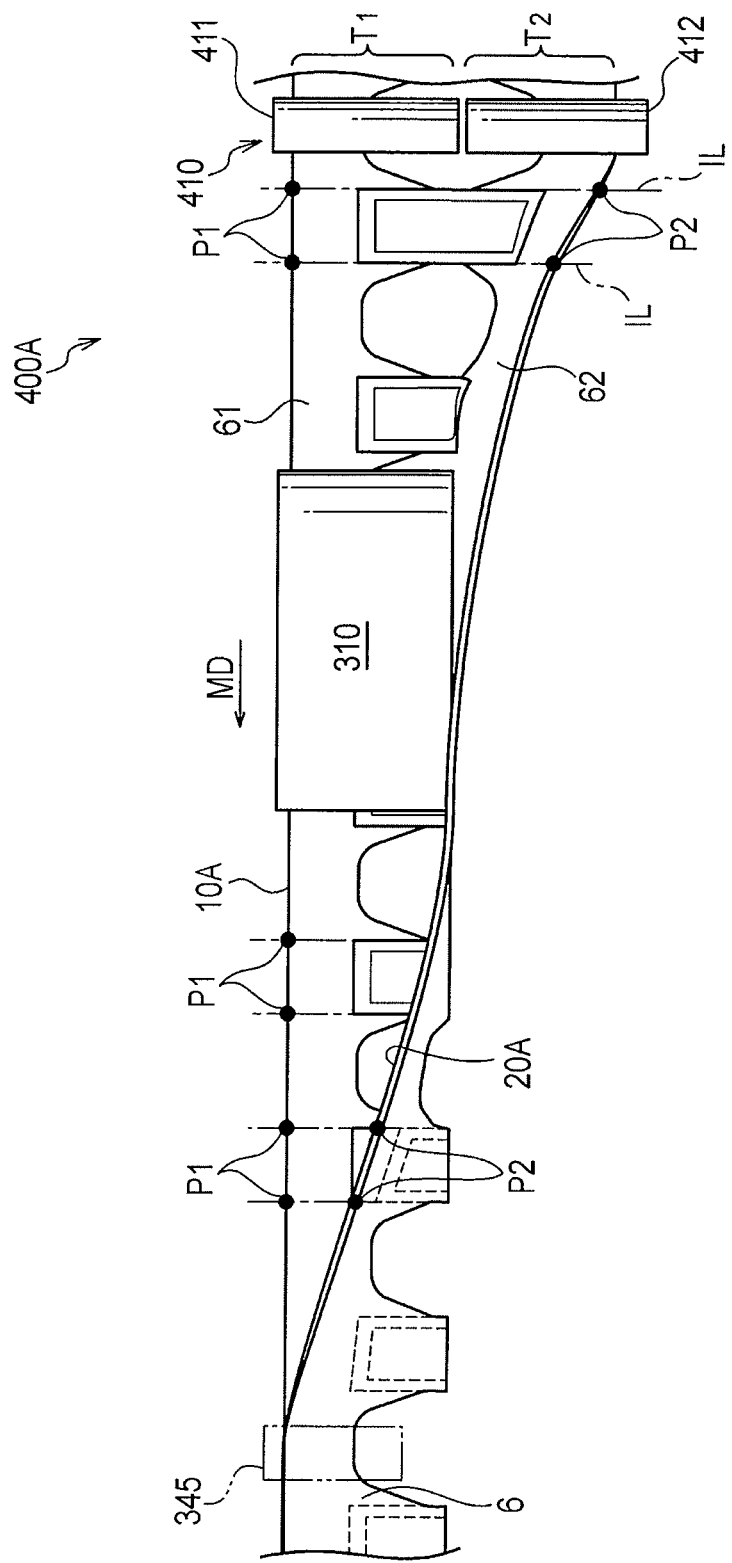
FIG. 9 is a plan view showing the vicinity of a press mechanism 400A according to a modified embodiment 1.

First, a configuration of a press mechanism 400A according to the modified embodiment 1 is described referring to drawings. FIG. 9 is a plan view showing the vicinity of the press mechanism 400A according to the modified embodiment 1.

According to the embodiment described above, the variable roll 410 in the press mechanism 400 has a length longer than a length along the cross direction from the side edge 10A to the side edge 20A, whereas a length of the variable roll 410 in the press mechanism 400A according to the modified embodiment 1 is shorter than the length along the cross direction CD from the side edge 10A to the side edge 20A.

Specifically, as shown in FIG. 9, the variable roll 410 includes a variable roll 411 and a variable roll 412. The variable roll 411 comes into contact with the first region T1 only, whereas the variable roll 412 comes into contact with the second region T2 only.

Similarly with the embodiment described above, the variable rolls 411 and 412 can move up and down respectively. That is, the position changer 420 moves the variable rolls 411 and 412 up and down respectively according to the amount of misalignment from the imaginary point P1 and the imaginary point P2 so as to change the first track length L1 and the second track length L2.

Meanwhile, the variable rolls 411 and 412 are described as being movable respectively. However, at least only either of the variable rolls may be moved, and only either of them may be provided. That is, the variable roll 410 may abut at least only one of the first region T1 and the second region T2.

Modified Embodiment 2

Next, a configuration of a press mechanism 400B according to the modified embodiment 2 is described referring to drawings. FIG. 10 is a side view showing the vicinity of the press mechanism 400B according to the modified embodiment 2.

According to the embodiment described above, the press mechanism 400 is provided between the conveyor roll 203 and the large-diameter roll 310, whereas, according to the modified embodiment 2, the press mechanism 400B is provided downstream of the large-diameter roll 310 in the machine direction MD.

Specifically, as shown in FIG. 10(a), the variable roll 410 includes the variable rolls 413 and 414. The variable roll 413 comes into contact with an upper surface of the first region T1, while the variable roll 414 comes into contact with a lower surface of the first region T1.

The variable rolls 413 and 414 are located among multiple conveyor belts 320. The variable rolls 413 and 414 hold the first region T1. The variable rolls 413 and 414 can move up and down respectively similarly with those according to the embodiment described above. That is, the position changer 420 moves the variable rolls 413 and 414 up and down according to the amount of misalignment between the imaginary points P1 and P2 so as to change the first track length L1 and the second track length L2.

Here, the variable rolls 413 and 414 do not necessarily hold the first region T1, and may hold the second region T2 as shown in FIG. 10(b) or may hold both the first region T1 and the second region T2.

Moreover, the variable roll 410 does not necessarily consist of two rolls but may consist of at least either of the rolls.

Modified Embodiment 3

Figure 11:
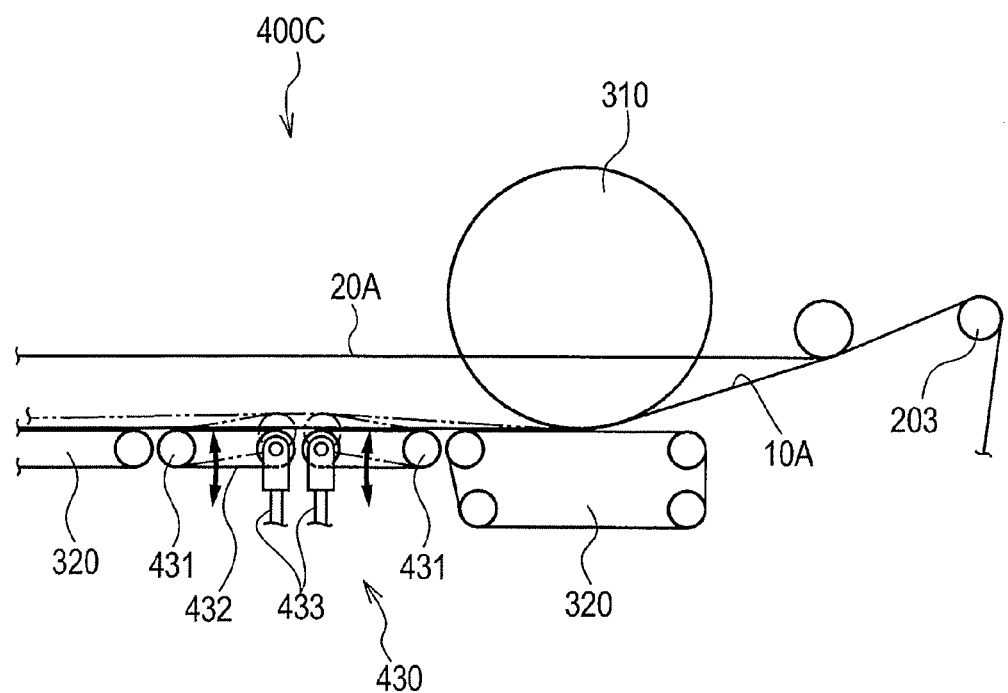
FIG. 11 is a side view showing the vicinity of a press mechanism 400C according to a modified embodiment 3.

Next, a configuration of a press mechanism 400C according to the modified embodiment 3 is described referring to drawings. FIG. 11 is a side view showing the vicinity of the press mechanism 400C according to the modified embodiment 3.

According to the embodiment described above, the press mechanism 400 includes the variable roll 410 and the position changer 420, whereas, according to the modified embodiment 3, the press mechanism 400C includes a variable belt conveyor 430.

Specifically, as shown in FIG. 11, the variable belt conveyor 430 is provided downstream of the large-diameter roll 310 in the machine direction MD. The variable belt conveyor 430 is located among multiple belt conveyors 320.

The variable belt conveyor 430 includes at least a conveyor belt 432 which turns around multiple rolls 431, a driving means (not shown) which makes the conveyor belt 432 turns around among multiple rolls 431, and a position changer 433 which moves at least one of rolls 431. The position changer 433 moves at least one of the rolls 431 up and down according to a misalignment between the imaginary points P1 and P2.

Other Embodiments

As described above, details of the present invention are disclosed through various preferable embodiments. However, it should not be understood that description and drawings constituting part of this disclosure limits the present invention. It will be apparent to those skilled in the art that various alternative embodiments, modifications and operational techniques can be made.

For example, an embodiment according to the present invention can be modified. Specifically, although the absorbent article 1 is described as being formed in combination of a front waistline portion 10, back waistline portion 20 and crotch portion 30 (so-called three-piece type), it is not limited thereto. Alternatively, the absorbent article 1 may be formed by integrating the front waistline portion 10, the back waistline portion 20 and the crotch portion 30 all together (so-called one-piece type). Moreover, configurations of the absorbent article 1 are not limited to those described in the embodiments, but may be set up appropriately in accordance with any intended use.

Furthermore, although the webs 61 and 62 are described as having property likely to contract (expand) in the cross direction CD by the waist gather 50A and the leg gather 60A, it is not limited thereto. Alternatively, the webs 61 and 62 may be made of a sheet having a self-contracting property.

Furthermore, although the webs 61 and 62 are described as being asymmetrical based on the central line CL, it is not limited to this. Alternatively, the webs 61 and 62 may be asymmetrical with respect to the center line CL.

Furthermore, although the first region T1 and the second region T2 are described as being folded into two in the folding step S4, there is no need to necessarily fold the first region T1 and the second region T2. For example, the first region T1 and the second region T2 may be folded into two with both of the regions substantially parallel with each other, and there may be some gap between the first region T1 and the second region T2.

Configuration of the folding machine is not limited to those described on the above embodiments, but may be set as appropriate in accordance with any intended use.

For example, although the web guide mechanism 300 is described as folding the second region T2 toward the first region T1 with the first region T1 as a horizontal surface (reference surface), the folding is not limited to this way. Alternatively, the web guide mechanism 300 may be configured to fold the first region T1 toward the second region T2 with the second region T2 as a horizontal surface (reference surface) or to overlay the first region T1 and the second region T2 each other (A-frame folding) at a vertical position with respect to a contact surface of the folding machine 100. In this case, the variable roll 410 may constitute the press roll 345. In this configuration, at least either of the first region T1 or the second region T2 can be pressed and phase misalignment adjustment can be performed simultaneously, whereby the manufacturing steps of the absorbent article 1 can be reduced.

Although the press mechanism 400 is described as being provided between the conveyor roll 203 and the press roll 345, position of the press mechanism 400 is not limited thereto. Obviously, the press mechanism may be provided before the front waistline portion 10 and the back waistline portion 20 are joined together in the joining step S5.

Furthermore, although the position changer 420 is described as moving the central axis 410A up and down in the axial view of the central axis 410A of the variable roll 410, its movement is not limited thereto. Alternatively, for example, the position changer 420 may tilt the central axis 410A in the vertical direction. Thus, the position changer 420 may move the central axis 410A in any direction so far as tension is applied to the webs 61 and 62.

Furthermore, although the cameras 421A and 421B are described as detecting the imaginary points P1 and P2 on an imaginary line IL passing a line along the cross direction of the absorber 4, the detecting is not limited to this way. Obviously, the cameras 421A and 421B may detect predetermined positions on an imaginary line passing a line along the cross direction CD of a member (surface sheet 2, for example) along the cross direction CD.

Furthermore, although the track detector 421 is described as consisting of the cameras 421A and 421B, it is not limited thereto. Alternatively, the track detector 421 may consist of one camera or an alternative device (sensor, for example) other than a camera which is capable of detecting a predetermined position.

As described above, the present invention obviously includes other various embodiments contained herein. Thus, technical scope of the present invention will be determined by specific invented items according to the scope of claims appropriate from above descriptions.

Note that, the entire content of Japanese Patent Application No. 2009-180205 (filed on Jul. 31, 2009) is incorporated herein by reference.

INDUSTRIAL APPLICABILITY

The present invention can provide a folding machine and a method for manufacturing an absorbent article, wherein adjustment of the phase misalignment can be simplified according to the web conveyance speed and web's characteristics, and thereby degradation in the manufacture quality of the absorbent article can be suppressed positively.

The invention claimed is:

1. A folding machine which overlays a first region and a second region of a successively conveyed web for an absorbent article with reference to a folding line parallel with a machine direction along a flow direction of a manufacturing process for the absorbent article, the first region formed between the folding line and one side edge of the web, the second region formed between the folding line and another side edge of the web, the folding machine comprising:
  a reference roll configured to come into contact with both the first region and the second region being flush with each other and to rotate with conveyance of the web;
  a web guide mechanism provided downstream of the reference roll in the machine direction, and configured to cause the first region and the second region to face each other with reference to the folding line so that an angle between the first region and the second region becomes smaller toward downstream; and
  a press mechanism provided downstream of the reference roll in the machine direction, and configured to press at least any one of the first region and the second region, wherein
the press mechanism includes a variable roll configured to come into contact with at least one of the first region and the second region, and a position changer configured to change a position of the variable roll,
the variable roll includes a central axis along a cross direction crossing the machine direction in a plan view of the web,
the position changer is configured to move the central axis of the variable roll,
the position changer includes:
  a detector configured to detect a first predetermined position in the one side edge and a second predetermined position in the other side edge; and
  a controller configured to control movement of the central axis of the variable roll when the controller determines that the first predetermined position and the second predetermined position are misaligned with each other in the machine direction, and
the press mechanism changes a pressing strength on the web to change at least any one of lengths of tracks in which the one side edge and the other side edge are respectively conveyed downstream of the reference roll in the machine direction.

2. The folding machine according to claim 1, wherein the variable roll is disposed between the reference roll and the web guide mechanism.

3. The folding machine according to claim 1, wherein the variable roll has a length longer than a width of the web in the cross direction and comes into contact with both the first region and the second region being flush with each other.

4. The folding machine according to claim 1, wherein
  the web guide mechanism includes a press-down mechanism configured to overlay the first region and the second region with each other by pressing at least one of the first region and the second region with the one side edge and the other side edge positioned in a predetermined positional relationship, and
  the press mechanism is provided between the reference roll and the press-down mechanism and changes at least one of lengths of tracks in which the one side edge and the other side edge are respectively conveyed between the reference roll and the press mechanism.

5. The folding machine according to claim 4, wherein the press-down mechanism comprises a press roll.

6. The folding machine according to claim 1, wherein the web guide mechanism overlays the first region and the second region with any one of the first region and the second region as a reference surface.

7. The folding machine according to claim 1, wherein when the controller determines that the first predetermined position is shifted downstream from the second predetermined position in the machine direction, the controller is configured to control the central axis of the variable roll to move up.

8. The folding machine according to claim 7, wherein when the controller determines that the first predetermined position is shifted upstream from the second predetermined position in the machine direction, the controller is configured to control the central axis of the variable roll to move down.

9. The folding machine according to claim 1, wherein when the controller determines that the first predetermined position is shifted upstream from the second predetermined position in the machine direction, the controller is configured to control the central axis of the variable roll to move down.

10. The folding machine according to claim 1, wherein
  the variable roll has a length shorter than a width of the web in the cross direction, and
  the variable roll is configured to come into contact with one of the first region and the second region without coming into contact with the other of the first region and the second region.

11. The folding machine according to claim 1, wherein the variable roll is arranged downstream of the web guide mechanism.

12. A method for manufacturing an absorbent article by overlaying a first region and a second region of a successively conveyed web for the absorbent article with reference to a folding line parallel with a machine direction along a flow direction of a manufacturing process for the absorbent article, the first region formed between the folding line and one side edge of the web, the second region formed between the folding line and another side edge of the web, the method comprising the steps of:
  causing the first region and the second region of the web to face each other with reference to the folding line by a web guide mechanism so that an angle between the first region and second region becomes smaller toward downstream, the web guide mechanism provided downstream of a reference roll in the machine direction, the reference roll coming in contact with the first region and the second region being flush with each other, and pressing at least one of the first region and the second region by a press mechanism provided downstream of the reference roll in the machine direction, wherein the step of pressing at least one of the first region and the second region includes changing a pressing strength on the web by the press mechanism to change at least one of lengths of tracks in which the one side edge and the other side edge are respectively conveyed downstream of the reference roll in the machine direction, the press mechanism includes a variable roll configured to come into contact with at least one of the first region and the second region, and a position changer configured to change a position of the variable roll, the variable roll includes a central axis along a cross direction crossing the machine direction in a plan view of the web, the position changer moves the central axis of the variable roll, the position changer includes a detector and a controller, and the method further comprises:
- detecting a first predetermined position in the one side edge and a second predetermined position in the other side edge by the detector; and
- controlling movement of the central axis of the variable roll when the controller determines that the first predetermined position and the second predetermined position are misaligned with each other in the machine direction.

13. The method according to claim 12, wherein when the controller determines that the first predetermined position is shifted downstream from the second predetermined position in the machine direction, the controller controls the central axis of the variable roll to move up.

14. The method according to claim 13, wherein when the controller determines that the first predetermined position is shifted upstream from the second predetermined position in the machine direction, the controller controls the central axis of the variable roll to move down.

15. The method according to claim 12, wherein when the controller determines that the first predetermined position is shifted upstream from the second predetermined position in the machine direction, the controller controls the central axis of the variable roll to move down.

16. The method according to claim 12, wherein
the variable roll has a length shorter than a width of the web in the cross direction, and
the variable roll comes into contact with one of the first region and the second region without coming into contact with the other of the first region and the second region.

17. The method according to claim 12, wherein
the variable roll is arranged downstream of the web guide mechanism.

18. A folding machine for overlaying a first region and a second region of a successively conveyed web for an absorbent article with reference to a folding line parallel with a machine direction along a flow direction of a manufacturing process for the absorbent article, the first region formed between the folding line and a first side edge of the web, the second region formed between the folding line and a second side edge of the web, the second side edge opposite the first side edge in a cross direction crossing the machine direction, the folding machine comprising:
- a reference roll configured to come into contact with both the first region and the second region being flush with each other and to rotate with conveyance of the web;
- a web guide mechanism provided downstream of the reference roll in the machine direction, and configured to cause the first region and the second region to face each other with reference to the folding line so that an angle between the first region and the second region becomes smaller toward downstream in the machine direction; and
- a press mechanism provided downstream of the reference roll in the machine direction, and including
  - a variable member configured to come into contact with at least one of the first region and the second region, and
  - a position changer configured to move the variable member for changing at least one of lengths of tracks in which the first side edge and the second side edge are respectively conveyed downstream of the reference roll in the machine direction, the position changer includes:
- a detector configured to detect a first predetermined position in the first side edge and a second predetermined position in the second side edge at a location downstream of the web guide mechanism; and
- a controller configured to control movement of the variable member when the controller determines that the first predetermined position and the second predetermined position are misaligned with each other in the machine direction.

19. The folding machine according to claim 18, wherein in response to a determination that the first predetermined position is shifted downstream from the second predetermined position in the machine direction, the controller is configured to control the variable member to move up.

20. The folding machine according to claim 19, wherein in response to a determination that the first predetermined position is shifted upstream from the second predetermined position in the machine direction, the controller is configured to control the variable member to move down.

* * * * *